United States Patent [19]
Hochberg et al.

[11] Patent Number: 5,955,273
[45] Date of Patent: Sep. 21, 1999

[54] USE OF THE H19 GENE AS A TUMOR MARKER

[75] Inventors: Abraham Hochberg, Jerusalem; Ilana Ariel, Givat Zeev, both of Israel

[73] Assignees: Yissum Research Development Company of the Hebrew University of Jerusalem; Hadasit Medical Research Services & Development Company Ltd., both of Jerusalem, Israel

[21] Appl. No.: 08/704,786

[22] PCT Filed: Mar. 6, 1995

[86] PCT No.: PCT/EP95/00823

§ 371 Date: Sep. 6, 1996

§ 102(e) Date: Sep. 6, 1996

[87] PCT Pub. No.: WO95/24503

PCT Pub. Date: Sep. 14, 1995

[30] Foreign Application Priority Data

Mar. 7, 1994 [IL] Israel ......................................... 108879

[51] Int. Cl.$^6$ .............................. C12Q 1/68; C07H 21/04; C12P 19/34
[52] U.S. Cl. ............................ 435/6; 435/91.2; 536/23.1; 536/24.31; 536/24.33
[58] Field of Search ............................... 935/2, 3, 77, 78; 435/6, 91.2; 536/23.1, 24.33, 24.5, 24.31

[56] References Cited

PUBLICATIONS

Rachmilewitz et al. FEBS Letters 309:25–28, Aug. 1992.
Prost et al. Proc. Annu. Meet. Am. Soc. Cln. Oncol. 12: A736, 1993.
Douc–Rasy et al. International Journal of Oncology 2:753–758 (May 1993).
Mutter et al. American Journal of Human Genetics 53:1096–1102 (Jul. 1993).
Yun Laboratory Investigation 67:653–664 (Nov. 1992).
Detta et al Molecular and Cellular Probes 5:537–443 (Dec. 1991).
Zhang et al. American Journal of Human Genetics 53:113–124 (1993).
Ogawa et. al. Nature 362:749–751 (Apr. 1993).
Hames et. al. editors Nucleic acid hybridisation IRL Press, Washington DC (1985) pp. 42, 179–187.
Bales et al Molecular and Cellular Probes 7:269–275 (Aug. 1993).
Rainer et al Nature 362:747–749 (Apr. 1993).
Saltman et al Genomics 16:726–732 (Jun. 1993).

*Primary Examiner*—Carla J. Myers
*Attorney, Agent, or Firm*—Pennie & Edmonds LLP

[57] ABSTRACT

An assay for diagnosing the presence or absence of certain malignancies and their grade and prognosis which comprises a) performing in situ hybridization of a tissue of the patient to be examined with a probe derived from the H19 gene and b) evaluating the results diagnosing the presence or absence of such malignancy and its severity. The probe used is derived from the H19 gene by a) subcloning at a suitable site in a plasmid, b) producing antisense RNA by transcription with a polymerase and c) labeling suitable fragments of the H19 RNA, such that after the hybridization, a signal for the diagnosis and establishment of the severity is produced. Suitable labels are radioactive or fluorescent labels, or color change reagent. Kits are provided for effecting such assays.

25 Claims, No Drawings

USE OF THE H19 GENE AS A TUMOR MARKER

There is provided an extremely sensitive assay for the early detection of human cancer, of various types. The assay is based on the use of a molecular marker, designated as Gene H19, which is used for in-situ hybridization of a tissue sample and for indicating the absence or presence of a cancer and its grading by a suitable marker (probe). Also, a kit for carrying out such an assay is provided.

Despite intensive therapeutic efforts cancer death rates are increasing. In the US they went up by 7 percent between 1975 and 1990. Should this trend continue, by the year 2000 every third individual in the western countries will harbor a potentially fatal malignancy. A major reason accounting for treatment failure is its administration to patients with a biologically advanced disease. A deceivingly small one cubic centimeter of tumor contains about a billion cancer cells. As a rule, patient prognosis—i.e., risk of recurrence and death, is directly correlated with the extent of the disease at the time of diagnosis: the more advanced the disease, the poorer the patient's chances are. Only a strategy leaning heavily on a) prevention and b) early detection could result in substantial gains. Tile leads indicating the importance of an early diagnosis come from analysis of US as well as of Japanese statistics. In the former, cancers of the urinary bladder (TCC) and of the uterine cervix and in the latter stomach cancer have shown reduced mortality. These achievements are due to early diagnosis and to screening of populations at risk. Current diagnostic tools, besides physical examination, are mainly imaging by (conventional or CT) X-rays and ultrasonography. Usually, their resolution power can detect lesions only if larger than one cubic cm. Biochemical testing of tumor products released into the blood stream, tumor "markers", is considerably more sensitive. Likewise, specific staining of biopsied tissues can detect minimal disease.

Genomic imprinting—the uniparental transmittance of a genetic trait—plays a pivotal role in embryogenesis and fetal development, and has been linked to tumorigenesis and human disease. H19 is an imprinted gene in human, expressed from the maternal allele. It is extensively transcribed early in embryogensis and in certain fetal tissues, and its expression is shut off in postnatal life. The expression of H19 parallels, in general, the expression of insulin-growth-factor 2, to which it is tightly linked on chromosome 11p15.5. The H19 gene does not encode for a protein and functions on an RNA molecule. Relaxation of imprinting of H19 has been demonstrated in Wilms' tumor as well as in troplioblastic neoplasia. We have studied the expression of H19 in several types of human cancer exhibiting features of tissues which expresses H19 in fetal life: transitional cell bladder tumors. Wilms' tumor and rhabdomyosarcoma, as well as gynogenetic germ cell tumors. Two low-grade transitional cell tumors of the urinary bladder did not express the gene, like in bladder mocosa of the adult. Prominent expression of H19 was evident in 3 intermediate-grade and 4 high-grade transitional cell carcinomas and in in-situ bladder carcinoma adjacent to invasive tumor. H19 was found to be expressed in nephrogenic rests in a kidney of aniridia syndrome and in Wilms' tumor, as well as in 4/6 cases of embryonal rhabdomyosarcoma. Expression of H19 was noted in epithelial and mesenchymal elements of immature ovarian teratoma which developed after excision of dermoid cyst, while the original tumor did not express the gene. Prominent expression of this gene was also noted in certain elements of testicular germ cell and stromal-sex cord tumors. Genomic imprinting is a newly discovered mechanism in genetics by which certain traits are selectively expressed either from the maternal or from the paternal genome. Genomic imprinting plays a pivotal role in early stages of embryogensis and implantation as well as in fetal development.

Am. J. Hum. Genet., (1993), 53: pp 1096–1102 discloses an assay for indicating the presence or absence of malignancies which comprises in-situ hybridization of a tissue of a patient (e.g. hydatidiform moles and ovarian teratoma) with a probe derived from the H19 gene and evaluating the results obtained.

Int. J. Oncol. (1993), 2: pp 753–758 relates to the expression of the human fetal BAC/H19 gene in invasive cancers.

Am. J. Hum. Genet. (1993), 53(1): pp 113–124 relates to imprinting of human H19, allele-specific CpG methylation, loss of the active allele in Wilms' Tumor and potential for somatic allele switching.

Nat. Genet., (1993 June) 4(2): 110–113 relates generally to genomic imprinting and gene activation in cancer.

Nature, (Apr. 22, 1993), 362 (6422): pp 747–749 relates to the relaxation of imprinted genes in human cancer, focussing on kindney and Wilms' tumors.

The invention relates to an assay for indicating the presence or absence of certain malignancies and their grading, which comprises in-situ hybridization of a tissue or of a cytologic specimen of the patient to be examined, with a probe derived from the H19 gene, and evaluating the results obtained. According to the present invention there is provided an extremely sensitive assay for the early detection of human cancer, of various types. The assay is based on the use of a molecular marker, designated as Gene H19, which is used for in-situ hybridization of a tissue sample and for indicating tile absence or presence of a cancer and its grading by a suitable marker (probe). Also provided a kit for carrying out such assay. As set out above, there has been identified a molecular marker, a gene designated as H19, located on chromosome 11 in the vicinity of several cancer related genes. According to the invention, an assay is provided, based on in-situ hybridization (ISH) technique to analyze tissue sections for H19 expression.

We identified a molecular marker, a gene designated H19, located on chromosome 11 at a vicinity to several cancer related genes. By in-situ hybridization (ISH) technique applied to tissue section, the probe can tell whether the tissue is H19 positive or negative.

We have studied, so far, the following malignancies: trophloblastic tumors, ovarian teratomas, Wilms' tumor, rhabodomyosarcome (a muscle tumor), carcinoma of the urinary bladder and testicular germ-cell and sex cord stromal tumors. In the bladder carcinoma expression was positively correlated with tumor grading and malignant potential. Additional common cancers, among which are breast, colon, lung, paricras, skin, kidney and prostate cancers, are currently being studied for H19 expression.

To investigate the association of H19 expression with neoplasia we examined its expression as demonstrated by in-situ hybridization in several human tumors and preneoplastic conditions. We have chosen tumors which share morphologic features and tissue-specific markers with tissues which express H19 in fetal life, especially those tumors known to be linked to chromosomal aberrations on the short arm of chromosome 11 in the malignant or premalignant state. We also looked at H19 expression in gynogenetic ovarian mature and immature teratomas.

TRANSITIONAL CELL BLADDER TUMORS

The transitional cell tumors, arising from the epithelium lining the urinary collecting system, is one of the most prevalent types of cancer in the human.

The histopathologic grading of transitional cell neoplasma is based on their resemblance to the normal tissue and correlates well with their biologic behavior, including the potential to become invasive.

Prominent expression of H19 was found in the transitional epithelium of the renal pelvis and ureter and of the urinary bladder of the fetus but not in the bladder mucosa of the adult.

No expression of H19 was detected in two cases of low grade well differentiated papillary (grade 1 out of 3) bladder carcinoma. Prominent expression was found in 3 intermediate grade (2) (one with submucosal invasion and one with muscularis invasion) and 4 cases of high grade (3) invasive bladder carcinoma.

Pronounced expression of H19 was also noted in carcinoma in-situ of the bladder mucosa adjacent to invasive cancer. These findings suggest that expression of H19 correlates with the stage of differentiation and hence with the invasive potential of transitional cell bladder carcinoma, and possibly can serve as a marker in cases of low to intermediate malignancy to indicate a more aggressive behavior.

WILMS' TUMOR

Wilms' tumor is a pediatric tumor of the kidney which resembles the fetal kidney and contains elements of the primitive metanepliric blastema differentiating to tubular and/or glomerular structures admixed with mesenchymal stroma. Wilms' tumor is associated with several hereditary disorders, among which are Beckwith-Wiedemann syndrome, hemihypertrophy and the aniridia syndrome.

The expression of H19 in the fetal kidney is prominent in the primitive metanephric blastema and is dramatically reduced with differentiation to tubular structures. In a kidney removed from a patient with aniridia syndrome. H19 expression was demonstrated in rests of metanephric blastema, while no expression was detected in the rest of the mature renal tissue. Expression of H19 was evident in Wilms' tumor, as already described (see above).

RHABDOMYOSARCOMA

Embryonal rhabdomyosarcoma is a solid pediatric tumor with morphologic and biochemical markers of striated muscle at early stages of differentiation. During embryogenesis pronounced H19 expression is found in primitive niesenchyme and myoblasts of the developing muscular system of the human embryo, but the expression is markedly reduced with differentiation of myotubes. With formation of myofibers in the fetus in the second trimester of pregnancy H19 expression is again abundant with residual low expression postnatally.

H19 expression was examined to 6 cases of embryonal rhabdomyosarcoma. The histologic diagnosis in all cases routinely included positive histocliemical staining for muscle markers and/or electron microscopic study. H19 was found to be expressed in 4/6 embryonal rhabdomyosarcoma.

OVARIAN TERATOMA

Two cases of immature ovarian teratoma following surgical excision of dermoid cyst (mature cystic teratoma) were examined for expression of H19, as well as one of the primary benign tumors. H19 was found to be expressed in mesodermal and endormal elements in immature teratoma, but not in the preceding dermoid cyst compared to mature tissue elements.

TESTICULAR GERM-CELL AND SEX-CORD-STROMAL TUMORS

Prominent expression of H19 was found in certain components non-seminomatous germ cell tumor, but no expression was disclosed in seminomas.

Expression of H19 was also found in stromal-sec-cord testicular tumors.

METHODS

1. Preparation of H19 probe for in-situ hybridization: A part of the human H19 gene (800bp) was subcloned onto a plasmid. In-vitro transcription with T7 RNA polymerase was used to produce antisense H19 RNA from linearized plasmid DNA using [$^{35}$S] UTP nucleotide, and was purified by ethanolic precipitation.

2. In-Situ Hybridization: Paraffin blocks were sectioned at 5 microns onto TESPA (Sigma) coated microscope slides. Sections were dewaxed with xylene, fixed by 0.2M paraformaidehyde solution and treated with proteinase K. The next steps were treatment with acetic acid anhybride and dehydration. Hybridization was performed using [$^{35}$S] RNA probes according to Standard procedures. The unhybridized probe was removed after 12 h of hybridization. The slides were exposed to a photographic emulsion for 4–6 days, developed using Kodak D19 developer and fixed with Kodak fixer. The slides were counterstained using Hematoxylin-eosin, examined and photographed using a light microscope under bright and dark field illumination. This method may be utilized for examination of histological and cytological slides from all tissues. To facilitate rapid laboratory examination the H19 antisense probe will be labeled with a fluorescentic tag or color which will shorten exposure tune to 24 h.

Fluorescentic labelling of another oncodevelopmental gene (IGF2) by a dye which emits fluorescent light at a different wavelength will allow visualization of both gene products on the same slide. Analysis of these slides requires only a fluorescence microcope. Some newly available commercial kits for in-situ hybridization combined with fluoro-labelled HI9 and IGF2 probes will comprise a user-friendly laboratory package.

We claim:

1. A method for detecting a bladder carcinoma cell in a tissue, comprising the steps of:
   (a) contacting said tissue with a probe that specifically hybridizes to the H19 gene or its complementary sequence; and
   (b) determining hybridization of the probe with a cell in said tissue, thereby detecting said cell as a bladder carcinoma cell in said tissue.

2. The method of claim 1 in which the probe is linked with a detectable label.

3. The method of claim 2 in which the label is a radioactive label.

4. The method of claim 2 in which the label is a fluorescent label.

5. The method of claim 2 in which the label is a colorimetric reagent.

6. The method of claim 2 in which the label is an enzyme.

7. The method of claim 1 in which the bladder carcinoma cell is of intermediate to high grade.

8. A method for detecting a sex cord stromal tumor cell in a tissue, comprising the steps of:
   (a) contacting said tissue with a probe that specifically hybridizes to the H19 gene or its complementary sequence; and
   (b) determining hybridization of the probe with a cell in said tissue, thereby detecting said cell as a sex cord stromal tumor cell in said tissue.

9. The method of claim 8 in which the probe is linked with a detectable label.

10. The method of claim 9 in which the label is a radioactive label.

11. The method of claim 9 in which the label is a fluorescent label.

12. The method of claim 9 in which the label is a colorimetric reagent.

13. The method of claim 9 in which the label is an enzyme.

14. A method for detecting an immature ovarian teratoma cell in a tissue, comprising the steps of:

(a) contacting said tissue with a probe that specifically hybridizes to the H19 gene or its complementary sequence; and (b) determining hybridization of the probe with a cell in said tissue, thereby detecting said cell as an immature ovarian teratoma cell in said tissue.

15. The method of claim 14 in which the probe is labeled with a detectable label.

16. The method of claim 15 in which the label is a radioactive label.

17. The method of claim 15 in which the label is a fluorescent label.

18. The method of claim 15 in which the label is a colorimetric reagent.

19. The method of claim 15 in which the label is an enzyme.

20. A method for detecting a rhabdomyosarcoma cell in a tissue, comprising the steps of:

(a) contacting said tissue with a probe that specifically hybridizes to the H19 gene or its complementary sequence; and (b) determining hybridization of the probe with a cell in said tissue, thereby detecting said cell as a rhabdomyosarcoma cell in said tissue.

21. The method of claim 20 in which the probe is labeled with a detectable label.

22. The method of claim 21 in which the label is a radioactive label.

23. The method of claim 21 in which the label is a fluorescent label.

24. The method of claim 21 in which the label is a colorimetric reagent.

25. The method of claim 21 in which the label is an enzyme.

* * * * *